United States Patent [19]

Sugarbaker

[11] Patent Number: 5,279,575
[45] Date of Patent: Jan. 18, 1994

[54] LOCKING PIVOTAL SURGICAL ORIFICE

[75] Inventor: David J. Sugarbaker, Brookline, Mass.

[73] Assignee: Brigham & Women's Hospital, Boston, Mass.

[21] Appl. No.: 929,729

[22] Filed: Aug. 13, 1992

[51] Int. Cl.[5] .............................................. A61M 5/00
[52] U.S. Cl. ........................................ 604/174; 606/1; 604/104
[58] Field of Search ................. 606/1; 604/104-109, 604/174, 175, 178

[56] References Cited

U.S. PATENT DOCUMENTS

| | | | |
|---|---|---|---|
| 766,336 | 8/1904 | Farrington | 604/104 |
| 1,434,964 | 11/1922 | Rose | 604/109 X |
| 4,069,826 | 1/1978 | Sessions et al. | 604/178 X |
| 4,315,513 | 2/1982 | Nawash et al. | 604/175 X |
| 5,007,900 | 4/1991 | Picha et al. | 604/175 X |
| 5,064,417 | 11/1991 | Andreussi | 604/175 |

*Primary Examiner*—Peter A. Aschenbrenner
*Attorney, Agent, or Firm*—Hamilton, Brook, Smith & Reynolds

[57] ABSTRACT

A device for use during endoscopic surgery for temporarily maintaining an open passageway through a body wall into a body cavity having a main hollow tube, a pair of extendable flukes pivotably mounted on the tube, a second hollow tube for camming the flukes open and clamping means for engagement with the skin of a patient and a third hollow tube for compressing the flukes in order that the device may be inserted into and removed from the incision.

19 Claims, 8 Drawing Sheets

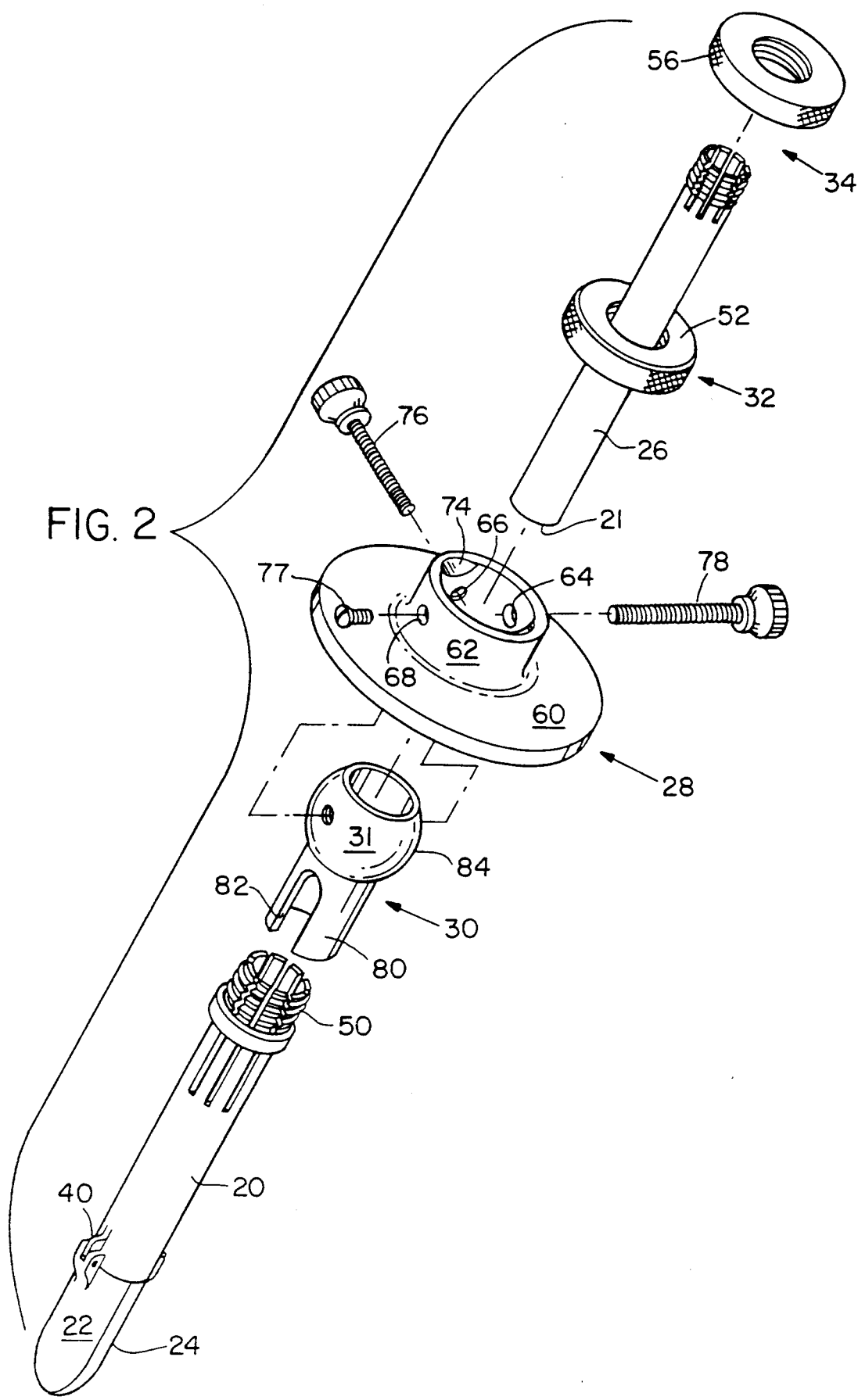

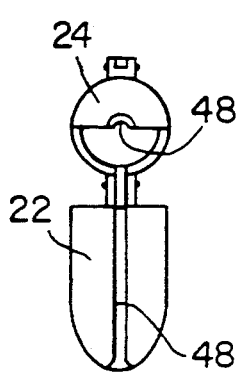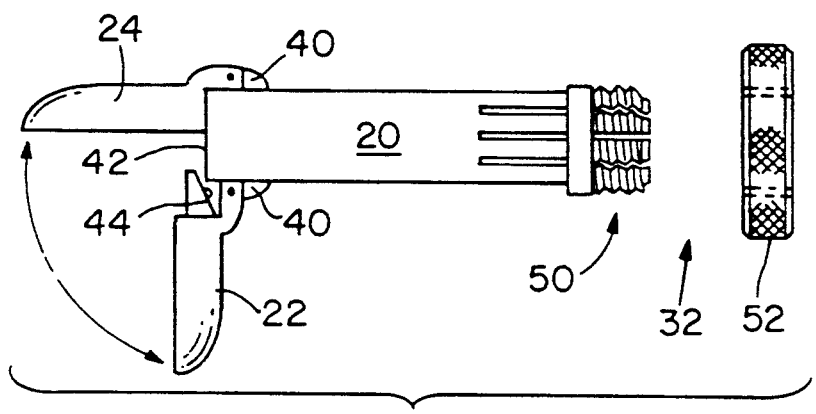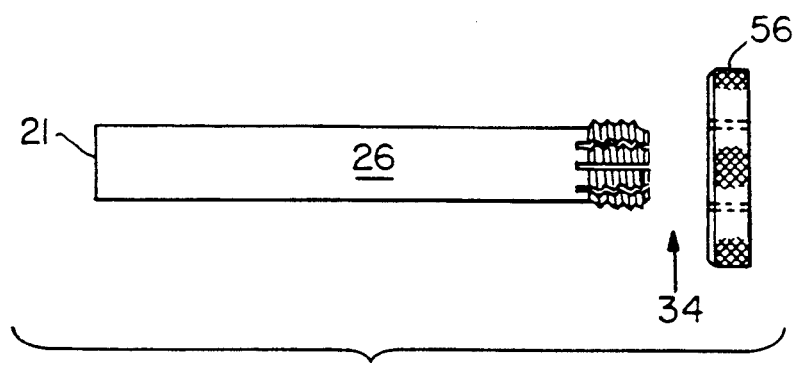
FIG. 4  FIG. 3
FIG. 5

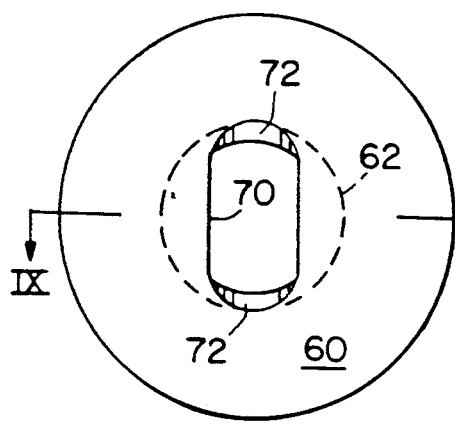
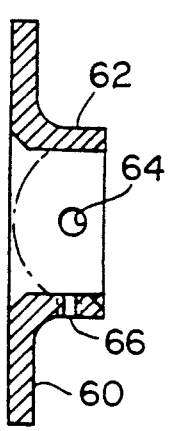
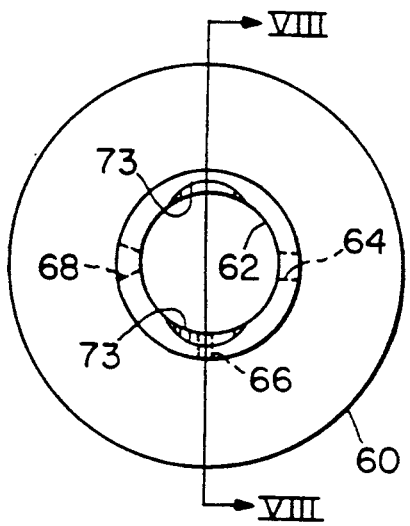
FIG. 6    FIG. 8    FIG. 7
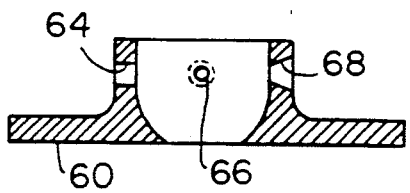
FIG. 9
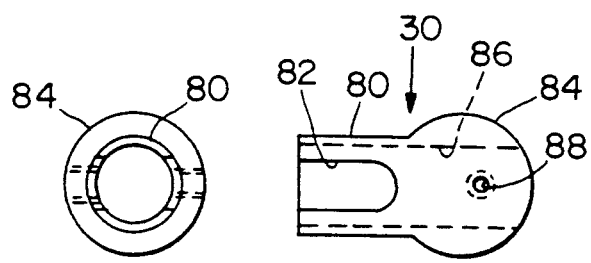
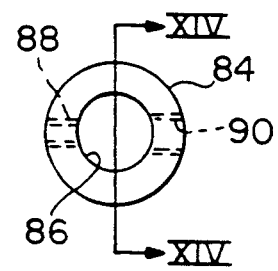
FIG. 11    FIG. 10    FIG. 12
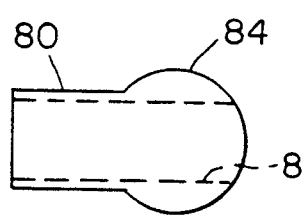
FIG. 13
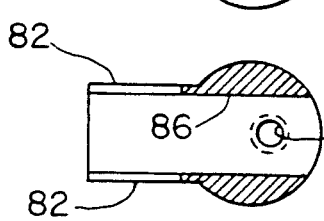
FIG. 14

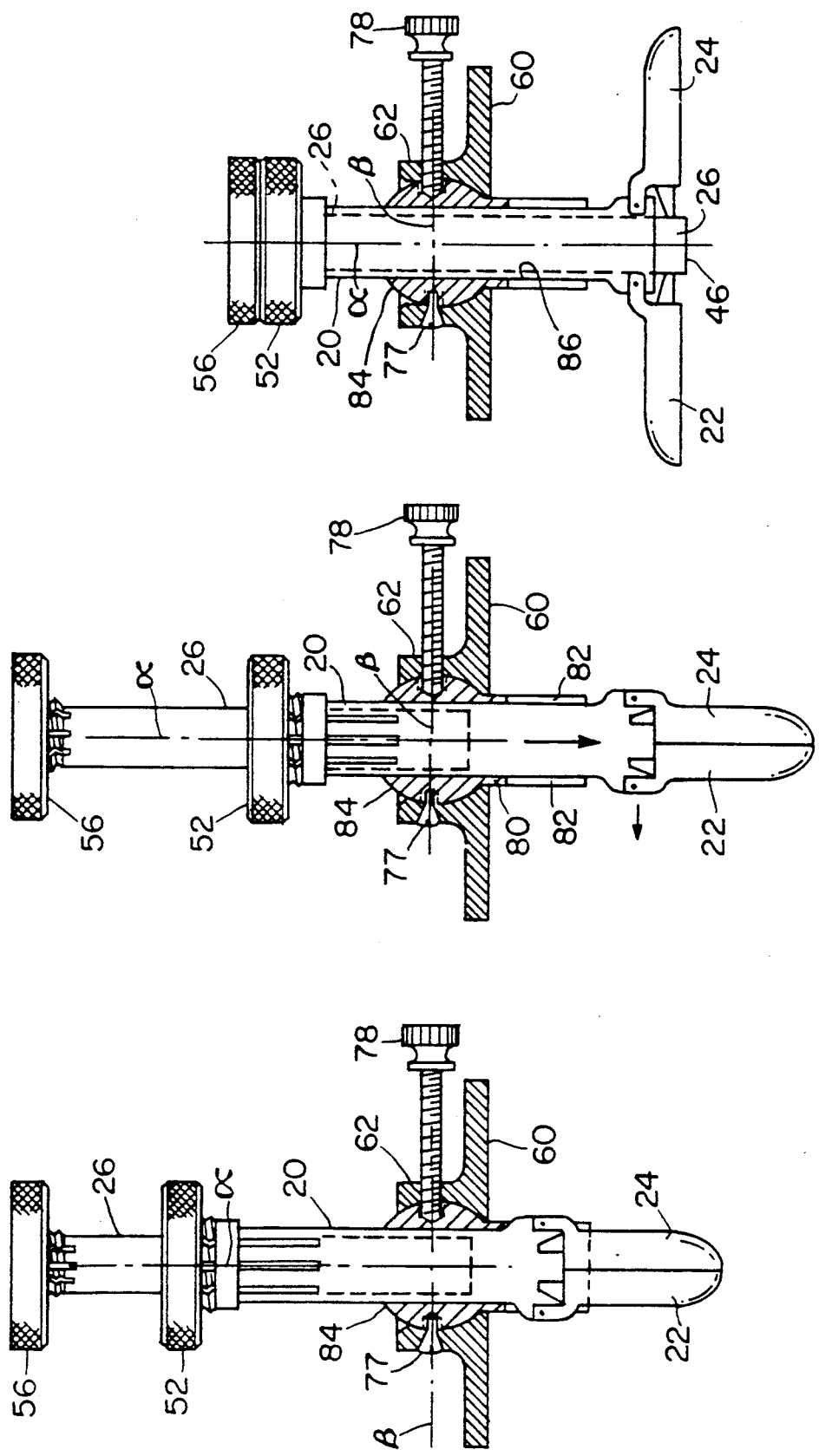

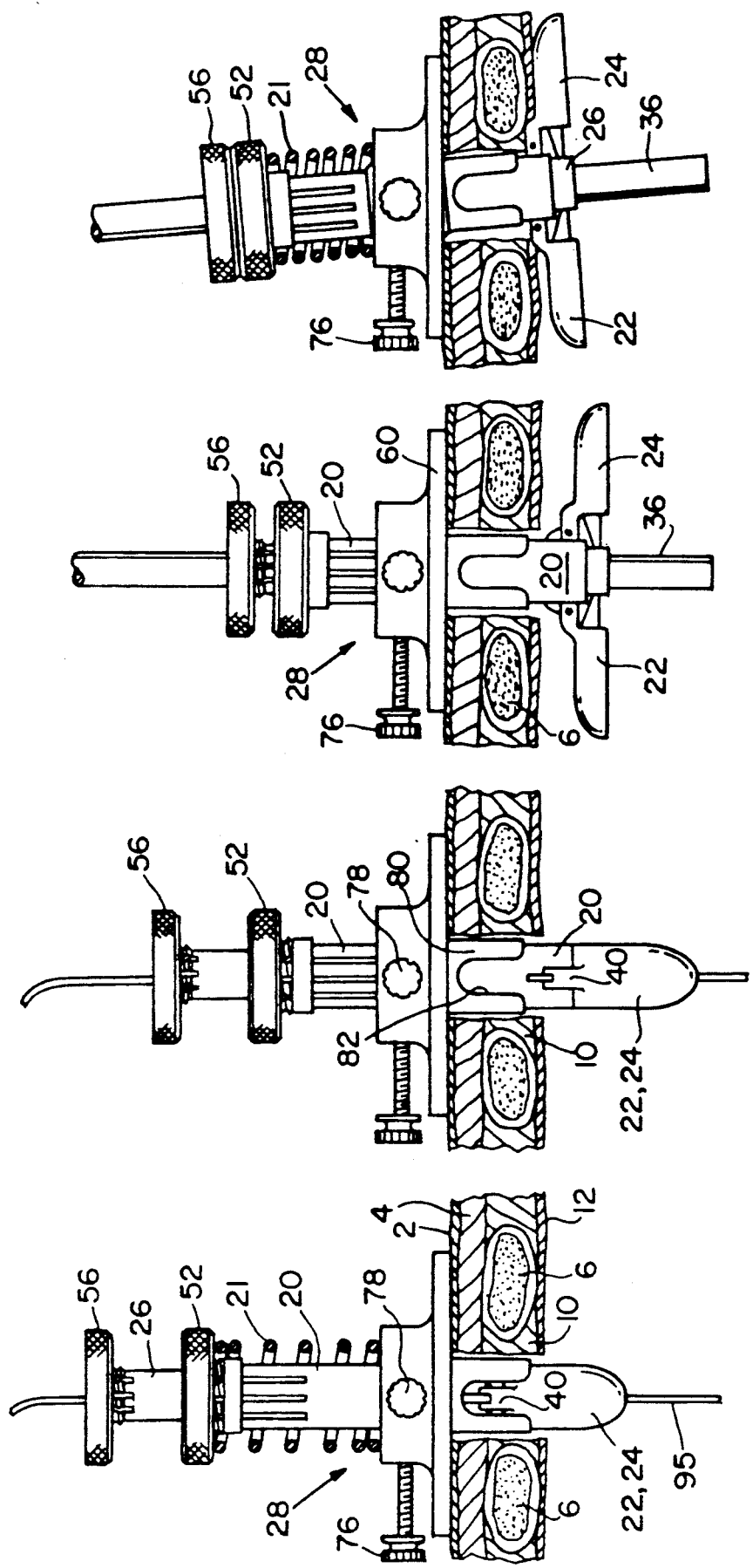

LOCKING PIVOTAL SURGICAL ORIFICE

BACKGROUND OF THE INVENTION

Great strides are being made in various areas of human surgery through the use of electronics and mechanical engineering principles. One such area is in endoscopic surgery or what is also called video surgery. The technique employs an external miniaturized video camera attached by fiber optic tubes to a light source and a telescopic lens, both of which are inserted as a unit through a small incision made in a patient's body. The camera projects a picture taken within the body and illuminated by the light source onto a video screen. Other surgical instruments such as scalpels, retractors and the like, which are specially designed for endoscopic surgery, are inserted through separate incisions in the patient.

The surgeon does not view the operative field per se, but rather views the picture on the video screen while performing surgery.

While the technique is referred to generically as endoscopic or video surgery, the equipment lends itself to a number of specific types of surgeries: anthroscopic (joints), angioscopic (blood vessels), laparoscopic (the abdomen), and thoracoscopic (the chest).

The benefits derived from this type of surgery are startling. The process, in some forms, is almost bloodless. Large ugly scars are eliminated. The process is much less traumatic and painful to the patient than open surgery. The patient leaves the hospital in a few days, and often the same day, as with some arthroscopic procedures.

One problem exists, however, in the use of modern endoscopic equipment: the location and alignment of the instruments relative to the surgical field are critical. The viewing lens and the light source must be maintained in a fixed, aligned position relative to the field. A fiber optic cable or rod inserted in a small incision through the skin and muscle is prone to misalignment and withdrawal unless it is held in place by a surgical assistant. This is not only tiring to the assistant if the surgical procedure is lengthy, but not totally satisfactory, since maintaining steadiness over lengthy periods is extremely difficult. Also the presence of the assistant and his hands in close proximity to where the surgeon is actually manipulating instruments can be bothersome to the surgeon.

Attempts to remedy the problem have been made by the provision of hollow guides which are inserted into the incision and through which the fiber optic rod or cable is passed. This is not totally satisfactory since the guides are prone to slip out of the incision requiring reinsertion and realignment.

It is to this problem that the present invention is directed.

SUMMARY OF THE INVENTION

The invention resides in a hollow guide which is inserted through an incision in a body wall and, thus, into a body cavity such as the abdomen or chest. The hollow guide is adjustable as to depth and adjustable relative to its own central axis to point or align the instrument, light source or camera lens relative to the operative field.

The guide clamps both internally and externally against the body wall to maintain alignment.

Another feature resides in the guide's orifice being able to releasably clamp or lock an instrument in the guide to prevent its withdrawal.

The device includes a main hollow tube which has a leading end insertable through the wall into the body cavity. A pair of extendable flukes are pivotably mounted on the leading end of the main hollow tube.

There is a second hollow tubular member which slides within the main hollow tube for camming the flukes into an extended position to engage the interior of the wall and for providing an open passageway into the cavity through which the endoscope or surgical instrument may be inserted.

There are primary clamping means movably mounted on the main hollow tube for engagement with the exterior of the body wall to clamp the device to the wall when the flukes are in their extended clamping position against the interior of the wall.

There is a third tube slidable on the main hollow tube which is movable into engagement with the flukes to compress them toward the main hollow tube to enable the device to be inserted into and removed from the body cavity through the small incision.

Means are provided for preventing movement between the second hollow tubular member and the main hollow tube when the second hollow tubular member has cammed the flukes into the extended position to prevent the flukes from being inadvertently collapsed.

There are also locking means for securing an instrument such as the endoscope in the second hollow tubular member to prevent its inadvertent removal.

The clamping means which engages the exterior of the body wall is rotatable on the main tubular body and is also pivotable on a curved surface on the third tube about an axis extending transversely of the main tubular member to permit axial adjustment of the device, thus to be able to point and maintain the instrument or endoscope at the operative field.

The clamping means and the element on which it pivots are secured to and slide with the second hollow tubular member.

The means for preventing movement between the second hollow tubular member and the main hollow tube may be a split collet and nut.

In like fashion, the medical instrument clamping means may be a split collet and nut on the second hollow tubular member.

The above and other features of the invention including various and novel details of construction and combinations of parts will now be more particularly described with reference to the accompanying drawings and pointed out in the claims. It will be understood that the particular locking, pivotal, surgical orifice embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 2 is an exploded view of the device shown in FIG. 1.

FIGS. 3, 4 and 5 are detailed viewed of the main hollow tube and the flukes.

FIGS. 6, 7, 8 and 9 are detailed views of the primary clamping means.

FIGS. 10-14 are detail views of the third slidable tube and the pivot means for the primary clamping means.

FIGS. 18-20 are detail views of the flukes being cammed from closed to open position.

FIGS. 21-24 are successive views of the device being inserted in a patient and being angularly adjusted.

DETAILED DESCRIPTION

The device embodying the invention is a locking, pivotal surgical orifice which is used during endoscopic surgery for temporarily maintaining an open passageway through a body wall into a body cavity through which instruments may be inserted and/or clamped. It will be understood that the locking, pivotal, surgical orifice is employable in numerous areas of the body. While it will be illustrated with respect to the chest, it may be employed, for example, in the same fashion in the abdominal cavity.

Figure 1:
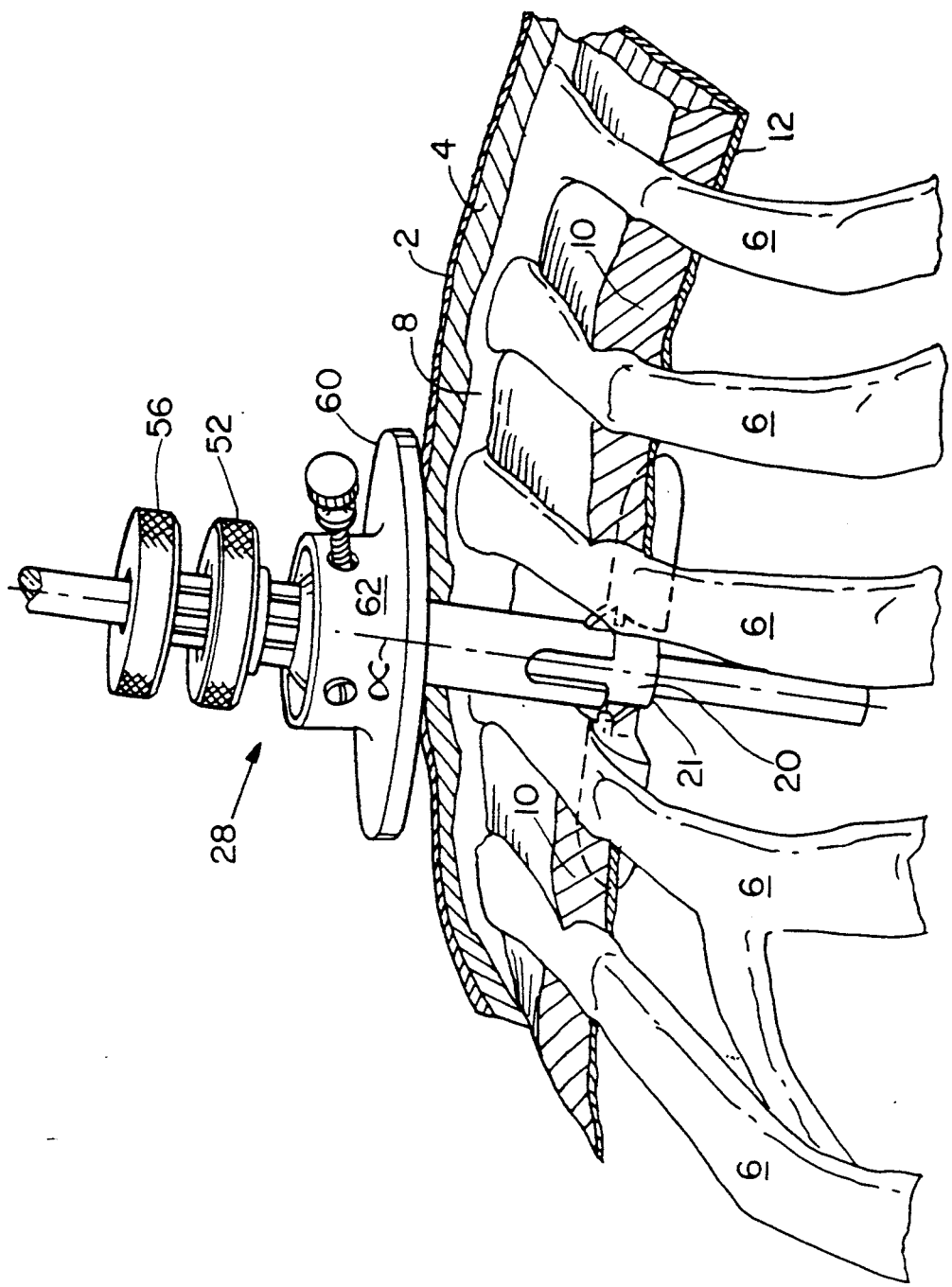
FIG. 1 is a perspective view of a human chest with portions removed for clarity into which a device embodying the present invention has been inserted.
Figure 15:
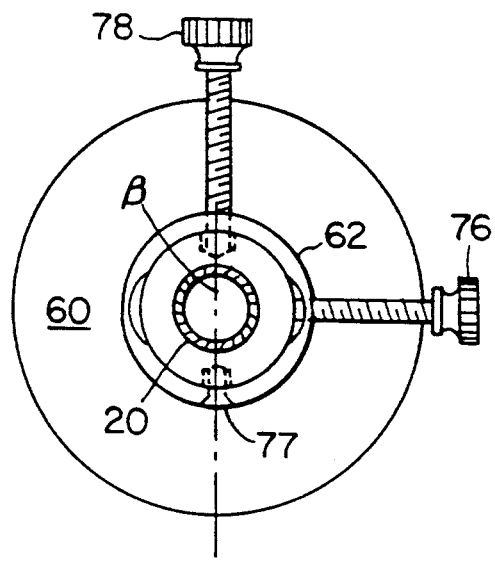
FIGS. 15-17 are detail views of the external clamping member and its pivot.
Figure 16:
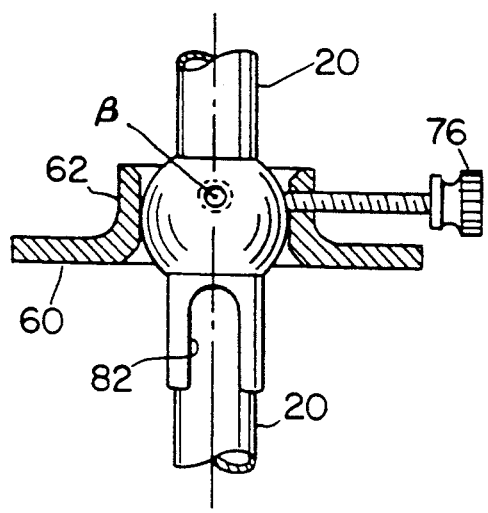
Figure 17:
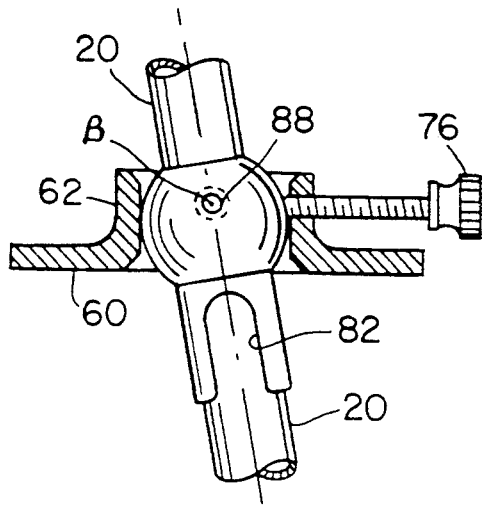

FIG. 1 is a view of the orifice device inserted into the chest cavity of a patient. A portion of the chest of the patient is shown in perspective and includes the outer layer of skin or the epidermis 2, the muscle 4 underlying the skin called the parietal pleura and which overlays the ribs 6, the sternum 8 to which the ribs are attached, the intercostal muscle 10 between the ribs and the membrane or parietal pleura 12 which lines the chest cavity.

The device includes a main hollow tube 20 having a central axis $a$ and a leading end 21 which is insertable through the body wall into the chest or abdominal cavity. In this case, it is insertable through a small incision through the intercostal muscle 10 which has been dilated or stretched to accommodate the size of the tube 20.

A pair of extendable flukes 22 and 24 are pivotably mounted on the main hollow tube 20. A second hollow tubular member 26 is slidable within the main hollow tube to cam the flukes 22, 24 into an extended position as seen in FIG. 1 to engage the interior of the body wall and for providing an open passageway into the body cavity.

External clamping means, generally indicated 28, are slidably and rotatably mounted on the main hollow tube 20 for engagement with the exterior of the body, in this case the epidermis of the chest. It clamps the device to the body wall when the flukes 22, 24 are in the extended clamping position against the interior of the body cavity.

A third tube 30 is slidable on the main hollow tube 20 into engagement with the flukes to compress them toward the main hollow tube 20 when the device is inserted into and removed from the body cavity. Tube 30 has a bulbous portion 31 which acts as a pivotal support for the clamping member 28.

There are additional clamping means, generally designated 32, for preventing movement between the second hollow tubular member 26 and the main hollow tube 20 when the second hollow tubular member has cammed the flukes into the extended position shown in FIG. 1.

Additional clamping means, generally designated 34, are employed for securing a medical instrument, in this instance, an endoscope 36 in the interior of the second hollow tubular member.

Referring next to FIGS. 3 through 5, the main hollow tube 20, the second hollow tubular member 26, the flukes 20, 22 and the secondary clamping means 32 and 34, respectively, will be described in greater detail.

The flukes 22, 24 are pivoted on ears 40 spaced 180° from each other and located adjacent the leading end 42 of the main hollow tube 20. Each fluke has an angular cam projection 44 which when, in the closed position as seen in FIG. 2, are engaged by the leading tubular end 46 of the second hollow tubular member 26 (FIG. 5) when it is pushed through the leading end 21 of the main tubular member 20. Upon engagement, the flukes 22, 24 are cammed into their open position (FIG. 1). Each fluke also includes a semicircular groove 48 which, when the flukes are in their closed position, creates a axial passageway for a surgical guidewire.

On the opposite end of the main hollow tube 20 is one of the secondary clamping members 32 comprising a split collet 50 which threadably engages a nut 52 together forming means 32 for gripping the second tubular member 26 and holding it in position in the main tube 20 to maintain the flukes in open position. Another clamping member 34 is located on the second hollow tubular member 26 for clamping an instrument in place also comprises a split collet 54 and a knurled nut 56.

Figure 26:
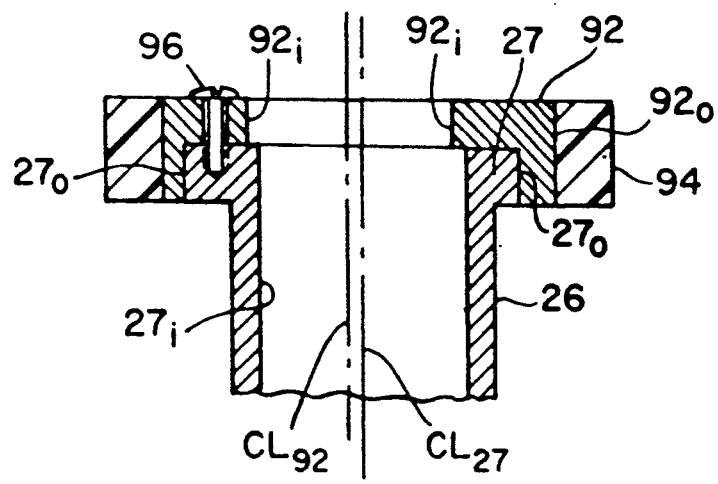
FIG. 26 is a section taken on the line XXVI—XXVI on FIG. 25.
Figure 25:
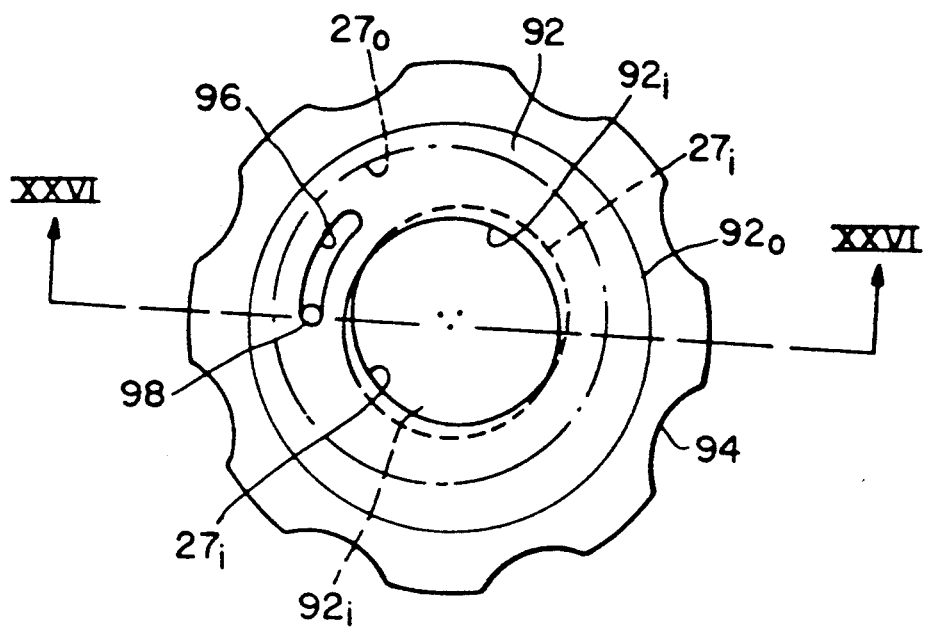
FIG. 25 is a plan view of an alternate construction for clamping a surgical instrument in the surgical orifice.

FIGS. 25 and 26 show an alternative construction to the clamping members 32 and 34. It will be illustrated with respect to the clamping member 34 which secures the medical instrument in the interior of the second hollow tube member 26. The alternative clamping member would operate similarly with respect to the clamping member 32.

A flange 27 is formed at the upper end of the hollow tubular member 26 and has an eccentric outer diameter $27_o$. An inverted flange 92, having an eccentric circular outer diameter $92_o$ is positioned above the flange 27. The flange 92 has an eccentric interior $92_i$. Where the diameters are considered to be eccentric, they are in fact circular but formed on separate center lines $CL_{27}$ and $CL_{92}$.

An arcuate slot 96 is formed in the flange 92 though which a pin 96 freely passes and is threadably attached to the surface of the flange 27. This permits the flange 92 to rotate approximately 45° or the arcuate length of the slot 96 relative to the flange 27, thereby causing the interior diameter $92_1$ and $27_i$ to move from a common center to eccentric centers thereby reducing the effective opening as seen in FIG. 25 thus being able to clamp in place an instrument positioned within the second hollow tubular member 26.

Details on the extended body clamping means 28 will be described initially with reference to FIGS. 6 through 9. It comprises a substantially circular flange 60 having an upwardly projecting circular collar 62 with three threaded holes 64, 66, 68. Passageway 68 is tapered. Passageway 66 is spaced 90° from holes 64 and 68.

The bottom of the flange 60 has an oblong opening 70 with arcuate cutout portions 72. The upper end of the collar 62 also has cutout arcuate portion 73 diametrically opposite arcuate cutaway portions 72. Screws 76 and 78 (FIG. 2) are threadedly received in the tapped holes 66 and 64, respectively, and set screw 77 is received in hole 68.

Referring next to FIGS. 10-14, the third slidable tube 30 will be described. Not only does this tube function to compress the flukes 22, 24 inwardly to the axis a for insertion and removal of the device, but it also serves as the pivot for the clamping flange 60. It includes a tubular portion 80 having a pair of diametrically arranged U-shaped slots 82, a ball 84 and a hollow tubular interior 86 slightly larger than the main hollow tube 20. A first threaded hole 88 is formed in the ball 84 opposite which a second larger threaded hole 90 is formed.

The clamping member 28 and the third sliding tube 30 are assembled and function as seen in FIGS. 15-20. The ball 84 on the sleeve 80 is placed in the neck 62 of the clamping flange 60. The second hollow tubular member 26 slides within the main hollow tube 20 which, in turn, slides within the interior 86 of the third tubular member 30. All three tubes pivot about the axis $\beta$ which passes through the aligned holes 64 and 68 in the neck 62 of the flange 60. The small set screw 77 in the hole 68 in the collar 62 enters the ball 84. A knurled screw 78 (FIG. 15) passes through the hole 64 in the neck 62 of the flange 60 and is threadably received in the hole 90 in the ball 84. This permits the flange 60 to pivot about the axis $\beta$ whereby the instrument may be tilted and adjusted from the FIG. 16 to the FIG. 17 position. In the desired position of adjustment, the screw 76 is tightened.

With the mechanism assembled as seen in FIGS. 18-20, the ball 84 is in the socket in the neck 62 of the clamping member. With the knurled clamping nut 52 loose, the second hollow tubular member 26 is free to be moved within the main hollow tube 20. With the hollow tube 20 in the FIG. 18 position, the clamping member 30 holds the flukes 22, 24 inwardly toward the axis a which is the center of the tube 20. The slots 82 in the sleeve portion 80 of the member 30 surround the ears 40 on which the flukes pivot. When the main hollow tube 20 is pushed downwardly through the third tube 30, the flukes 22, 24 including the ears 40 emerge from the slots 82 and are free to be opened as seen in the FIG. 19 position. The second hollow tubular member 26 is then moved downwardly until its leading edge 46 engages the camming members 44 on the flukes 22 spreading the flukes to the FIG. 20 position. Thereafter the knurled nut 52 is tightened on the split collet 50 maintaining the second hollow tubular member 26 in the FIG. 20 position.

Initially, the surgeon makes a small incision through the skin to the intercostal muscle 10 and the parietal pleura 12 passing between the ribs 6. The incision is then dilated and a guidewire 95 is inserted. With the sleeve portion 80 of the third slidable tube 30 maintaining the flukes 22, 24 in place, the instrument is inserted into the incision and down the guidewire 35 as seen in FIG. 21. At this time, the clamping nuts 52 and 56 are loose.

The surgeon continues to insert the main hollow tube 20 until the flukes 22, 24 and the ears emerge from the slots 82 in the sleeve portion 80 as seen in FIG. 22.

Preferably, the insertion is made with the ears and the flukes in the FIG. 21 and 22 positions, that is, not extending toward the ribs. This is to avoid any displacement of the ribs or causing excess pressure on the ribs.

Thereafter, the surgeon rotates the flukes 22, 24 by turning the main hollow tube 20 to the FIG. 23 position such that the flukes extend transversely of the ribs 6. He then draws the tube 20 slightly upwardly until the flukes engage the ribs. With the flange 60 of the clamping member 28 in engagement with the skin, the surgeon or his assistant inserts the instrument such as the fiber optic endoscope 36 and adjusts its angular orientation. The nut 56 is then tightened to maintain the endoscope firmly within the second hollow tubular member 26 and the knurled screw 76 is tightened to maintain the device in the desired angular orientation as represented by FIG. 24.

As an optional feature, a spring 21 may be employed as seen in FIGS. 21 and 24 to urge the flange 60 against the skin. The spring is located around the main hollow tube 20 and bears against the clamping nut 52.

It will be understood that a plurality of such devices may be employed during the operation and that the operation may be performed in other areas than the chest as, for example, the abdomen. Generally speaking, the device into which the endoscope is inserted will remain in place throughout the operation. However, with other devices in place, the surgeon may insert various operating instruments such as scissors, retractors, retrievers, or the like, while watching the entire operation on the video screen.

I claim:

1. A device for use during endoscopic surgery for temporarily maintaining an open passageway through a body wall into a body cavity comprising:
   a main hollow tube having a leading end insertable through the wall into the cavity,
   a pair of extendable flukes pivotably mounted on the leading end of the main hollow tube,
   a second hollow tubular member slidable within the main hollow tube for camming the flukes into an extended position to engage the interior of the wall and for providing an open passageway into the cavity, and
   clamping means movably mounted on the main hollow tube for engagement with the exterior of the body wall to clamp the device to the wall when the flukes are in the extended clamping position against the interior of the wall.

2. A device for use during endoscopic surgery for temporarily maintaining an open passageway through a body wall into a body cavity comprising:
   a main hollow tube having a leading end insertable through the wall into the cavity,
   a pair of extendable flukes pivotably mounted on the leading end of the main hollow tube,
   a second hollow tubular member slidable within the main hollow tube for camming the flukes into an extended position to engage the interior of the wall and for providing an open passageway into the cavity,
   clamping means movably mounted on the main hollow tube for engagement with the exterior of the body wall to clamp the device to the wall when the flukes are in the extended clamping position against the interior of the wall, and
   a third tube slidable on the main hollow tube into engagement with the flukes to compress them toward the main hollow tube to enable the device to be inserted into and removed from the body cavity.

3. A device for use during endoscopic surgery for temporarily maintaining an open passageway through a body wall into a body cavity comprising:
   a main hollow tube having a central axis and a leading end insertable through the wall into the cavity, a pair of extendable flukes pivotably mounted on the leading end of the main hollow tube, a second hollow tubular member slidable within the main hollow tube for camming the flukes away from the central axis and into an extended position to engage the interior of the wall and for providing an open passageway into the cavity, clamping means movably mounted on the main hollow tube for engagement with the exterior of the body wall to clamp the device to the wall when the flukes are in the extended clamping position against the interior of the wall, a third tube slidable on the main hollow tube into engagement with the flukes to compress them toward the central axis of the main hollow tube to enable the device to be inserted into and removed from the body cavity, and means for pivoting the clamping means relative to the central axis to adjust the angle of the device relative to the body wall.

4. Device according to claim 1 wherein there are means for preventing movement between the second hollow tubular member and the main hollow tube when the second hollow tubular member has cammed the flukes into the extended position.

5. Device according to claim 2 wherein there are means for preventing movement between the second hollow tubular member and the main hollow tube when the second hollow tubular member has cammed the flukes into the extended position.

6. Device according to claim 3 wherein there are means for preventing movement between the second hollow tubular member and the main hollow tube when the second hollow tubular member has cammed the flukes into the extended position.

7. Device according to claim 1 wherein there are means for securing a medical instrument in the second hollow tubular member.

8. Device according to claim 2 wherein there are means for securing a medical instrument in the second tubular member.

9. Device according to claim 3 wherein there are means for securing a medical instrument in the second tubular member.

10. Device according to claim 1 wherein the clamping means is rotatable on the main tubular body and pivotable about an axis extending transversely of the main tubular body.

11. Device according to claim 2 wherein the clamping means is rotatable on the main tubular body and pivotable about an axis extending transversely of the main tubular body.

12. Device according to claim 3 wherein the clamping means is rotatable on the main tubular body and pivotable about an axis extending transversely of the central axis of the main tubular body.

13. Device according to claim 3 wherein the clamping means and the means for pivoting it are secured to and slide with the second hollow tubular member.

14. Device according to claim 4 wherein the means for preventing movement is a split collet and nut.

15. Device according to claim 5 wherein the means for preventing movement is a split collet and nut.

16. Device according to claim 6 wherein the means for preventing movement is a split collet and nut.

17. Device according to claim 7 wherein the medical instrument clamping means is a split collet and nut on the second hollow tubular member.

18. Device according to claim 8 wherein the medical instrument clamping means is a split collet and nut on the second hollow tubular member.

19. Device according to claim 9 wherein the medical instrument clamping means is a split collet and nut on the second hollow tubular member.

* * * * *